US008588883B2

(12) United States Patent
Jadidi et al.

(10) Patent No.: US 8,588,883 B2
(45) Date of Patent: Nov. 19, 2013

(54) ELECTRODE ASSEMBLIES AND BRUXISM MONITORING APPARATUS

(75) Inventors: Faramarz Jadidi, Hasselager (DK); Claus Steen, Silkeborg (DK)

(73) Assignee: Sunstar Suisse SA, Etoy (CH)

( * ) Notice: Subject to any disclaimer, the term of this patent is extended or adjusted under 35 U.S.C. 154(b) by 517 days.

(21) Appl. No.: 12/679,034

(22) PCT Filed: Sep. 22, 2008

(86) PCT No.: PCT/DK2008/050230
§ 371 (c)(1), (2), (4) Date: Jan. 13, 2011

(87) PCT Pub. No.: WO2009/036769
PCT Pub. Date: Mar. 26, 2009

(65) Prior Publication Data
US 2011/0118581 A1    May 19, 2011

(30) Foreign Application Priority Data

Sep. 21, 2007 (GB) .................................. 0718486.4
Sep. 21, 2007 (GB) .................................. 0718487.2

(51) Int. Cl.
*A61B 5/0488* (2006.01)
*A61B 5/0492* (2006.01)

(52) U.S. Cl.
USPC ............ 600/372; 600/393; 600/546; 600/590

(58) Field of Classification Search
USPC .................................. 600/372, 393, 546, 590
See application file for complete search history.

(56) References Cited

U.S. PATENT DOCUMENTS

| 4,233,987 | A | * | 11/1980 | Feingold ........................ 600/382 |
| 4,669,477 | A | | 6/1987 | Ober |
| 4,715,367 | A | * | 12/1987 | Crossley ......................... 600/27 |
| 5,772,591 | A | | 6/1998 | Cram |
| 6,270,466 | B1 | * | 8/2001 | Weinstein et al. ............ 600/590 |
| 6,638,241 | B2 | * | 10/2003 | Yerushalmy .................... 604/31 |
| 7,130,673 | B2 | * | 10/2006 | Tolvanen-Laakso et al. . 600/383 |

FOREIGN PATENT DOCUMENTS

WO    WO 2004/087258    10/2004

* cited by examiner

*Primary Examiner* — Lee S Cohen
(74) *Attorney, Agent, or Firm* — Gifford, Krass, Sprinkle, Anderson & Citkowski, P.C.

(57) ABSTRACT

The invention relates to an apparatus for monitoring muscle activity related to bruxism, said apparatus comprising:—an electrode assembly for providing signals indicative of said muscle activity, means for processing said signals in order to detect said bruxism, and means for providing a feedback signal in response to detecting said bruxism; wherein said electrode assembly comprises three electrodes in a fixed spatial relationship one to another, each electrode having a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm.

20 Claims, 2 Drawing Sheets

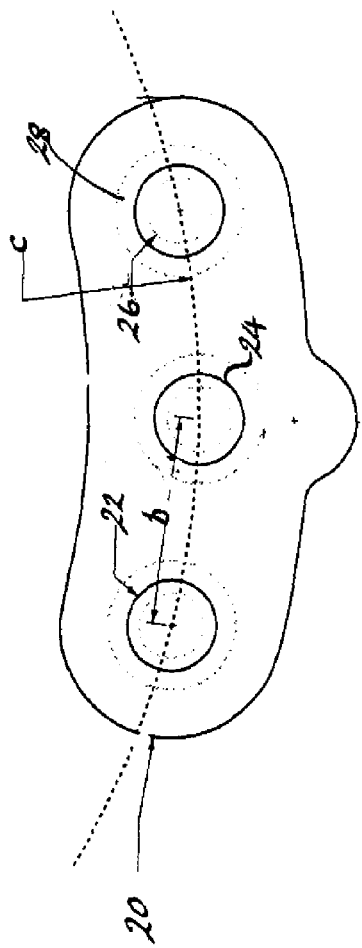
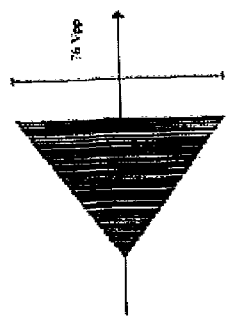
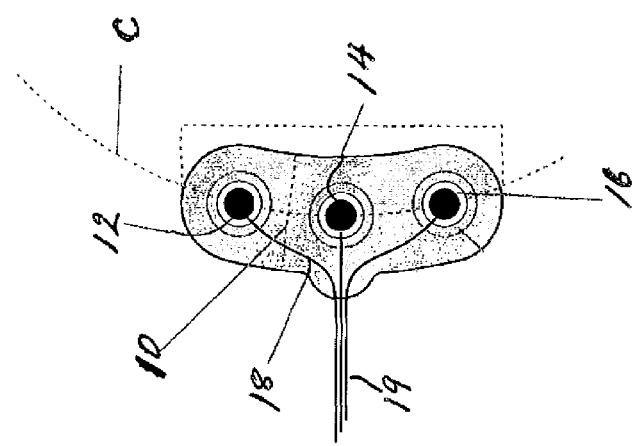

Stimulation blockdiagram :

ELECTRODE ASSEMBLIES AND BRUXISM MONITORING APPARATUS

CROSS-REFERENCE TO RELATED APPLICATIONS

This application is the U.S. national phase of PCT/DK2008/050230 filed Sep. 22, 2008, which claims priority of Great Britain Patent Application Nos. 0718486.4 and 0718487.2 filed Sep. 21, 2007.

The present invention relates to a method and an apparatus for monitoring activity of the temporal and/or masseter muscle, in particular temporal and/or masseter muscle activity due to bruxism.

Bruxism is a condition characterised by powerful jaw movements without any real function and which take the form of involuntary grinding movements of the teeth during strong clenching. This affliction may cause serious dental damages such as for example wearing of the teeth, damage to lips and the tongue, lose teeth, and gingival pockets. Bruxism is often in addition also associated with pain in the back of the head and chronic headache.

Chronic bruxism is divided into nocturnal and daytime bruxism. Daytime bruxism is characterized by being a conscious clenching of upper and lower jaws and grinding of the teeth, although dominated by the latter. Since night-time bruxism is unconscious it may normally only be perceived by those in the surroundings (for example relations) as an unpleasant squeaky noise. Daytime bruxism may often be provoked by exposure to stress. It may be relieved relatively easily by drawing the attention of the person to the bruxism. Night-time bruxism is often alleviated by protecting the teeth with a splint.

Attempts have been made to detect night time bruxism by the use of an electronic monitoring apparatus which provides a feedback or alarm signal when bruxism is detected. WO2004/0872258 describes a sophisticated and effective form of such apparatus in which EMG (electromyography) signals are picked up from an electrode on the skin and are analysed electronically. The feedback signal is a stimulation signal sent back to the skin via the same electrodes. This signal is intended to be sufficient to have an effect on bruxism but not so strong as to wake the patient.

SUMMARY OF THE INVENTION

In WO2004/0872258 it was disclosed that EMG signals for monitoring bruxism may be derived from the temporal muscle or from the masseter muscle. Previous work in this field has generally used the masseter muscle. This is more accessible as the temporal muscle has most of its bulk above the hair line and EMG signals available from that portion outside the hair line are much weaker and more difficult to process than those available from the masseter muscle. However masseter is only accessible through the skin at the cheek and jaw of the patient and electrodes located at the cheek and/or jaw may be unpleasant for a patient during sleep. A electrode assembly, preferably small, near the temple of the patient where the front edge of the temporal muscle is accessible is more pleasant for a patient. Therefore it is an object of the invention to provide an electrode assembly specially suited for gathering signals from the front edge of the temporal muscle, i.e. a small electrode assembly which is pleasant to the patient, however all together efficient for sensing and/or impacting the temporal muscle.

This is achieved by an apparatus for monitoring muscle activity related to bruxism, said apparatus comprising:

an electrode assembly for providing signals indicative of said muscle activity, means for processing said signals in order to detect said bruxism, and means for providing a feedback signal in response to detecting said bruxism activity;

wherein said electrode assembly comprises three electrodes in a fixed spatial relationship one to another, each electrode having a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm.

The invention furthermore relates to a method for monitoring activity of the temporal muscle, in particular activity of the temporal muscle due to powerful teeth and/or jaw clenching, said method comprising the steps of:

providing signals indicative of activity of said temporal muscle by means of an electrode assembly having three electrodes in a fixed spatial relationship wherein each electrode has a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm, processing said signals in order to detect temporal muscle activity, and providing a feedback signal in response to detecting the temporal muscle activity.

In a further aspect the feedback signal is provided to reduce the activity of the temporal muscle.

In yet another aspect of the invention the monitored activity of the temporal muscle is due to bruxism, whereby bruxism is monitored by the method according to the invention.

Furthermore, the method regards preventive treatment of bruxism, preferably by means of the feedback signal provided to reduce the activity of the temporal muscle.

There may be more than three electrodes, but three is the preferred number. The electrodes may be mounted on a common substrate. It will be appreciated that the electrodes may each comprise a solid conductive electrode member provided with a respective patch of conductive gel in said assembly, in which case it will be the area of the gel that defines the contact area of the electrode rather than the size of the electrode member.

The area of an electrode member in contact with such a gel patch may be approximately from 5% to 100% of the electrode contact area (i.e. the gel patch area), in some cases 25% to 75%, e.g. about 50%.

In order to fit well along the front edge of the temporal muscle, the electrodes may be arranged to lie on a line which is a straight line. However, in order to match the shape of the temporal muscle near the temple of the patient the electrodes may be arranged to lie on a line which is an arc of a circle having a radius of from 50 mm or more. Preferably, such a circle has a radius of 60 mm or more, such as from 60-200 mm, for instance about 70 mm. Preferably, centres of the contact areas of such electrodes lie on such lines. Thus, the electrodes may be arranged such that centres of said electrodes and of the electrode contact areas and/or of the electrode members lie on a line which is an arc of a circle having a radius of from 50-500 mm, more preferably from 60-200 mm, e.g. about 70 mm.

The electrode contact areas may extend along or on a said line a distance of from 1 to 10 mm from one side to an opposite side of the electrode contact area and may extend transversely of a said line by a distance of from 1 to 10 mm from one side to an opposite side of the electrode contact area, the maximum distance along said line from an edge of a first said electrode contact area to an opposite edge of the furthest away of the other two electrode contact areas being not more than 60 mm, more preferably 50 mm. Preferably, the contact areas of the electrodes may extend along or on said line a distance of from 3 to 7 mm from one side to an opposite side of the electrode contact area. Similarly, the contact areas of the electrodes may extend transversely of said line by a distance of from 3 to 7 mm from one side to an opposite side of the electrode contact area.

Thus, for instance the electrode contact areas may be circular and of diameter from 2-20 mm, more preferably from 5-15 mm, e.g. about 10 mm, and the electrode members may also be circular having a diameter of from 1-10 mm, more preferably from 3 to 7 mm, e.g. about 5 mm. The electrode contact areas and the electrode members may be of other shapes having equivalent areas to those described above.

Preferably, the maximum distance along said line from an edge of a first said electrode contact area to an opposite edge of the furthest away of the other two electrode contact areas is from 20 to 50 mm, more preferably from 30 to 50 mm, e.g. about 40 mm.

Whilst the generally linear configuration of the electrodes is preferred, optionally the contact areas of the electrodes may be arranged in a triangular arrangement in which the longest side of the triangle so defined is not more than 40 mm, more preferably not more than 30 mm.

Preferably, said means for processing said signals in order to detect said bruxism activity measures the amplitude of EMG signals received from said electrode assembly at least one predetermined frequency. The frequency content of the received signals is preferably analysed by Fourier analysis, suitably using a DFT (Digital Fourier Transform), particularly an FFT (Fast Fourier Transform) signal analysis. This can produce a power spectrum from which specific frequency bands may be selected to form the basis of the measurement.

It is furthermore an object of the invention to provide that the apparatus can distinguish between muscle activity due to bruxism and normal muscle activity. This is achieved by letting said device be operable in a set-up mode and in a use mode. In said set-up mode the apparatus is configured to accept an input defining said at least one predetermined frequency and in said use-mode the apparatus detects bruxism episodes by measuring the amplitude of EMG signals at least one frequency received from said electrode assembly.

In order to determine for a given user the ideal frequency or frequencies to measure so as reliably to determine the occurrence of a bruxism episode, it is preferred that said device is operable in said set-up mode to measure a first power spectrum of signals received from said electrode assembly when a user carries out a first exercise simulating bruxism muscle activity (such as teeth clenching) and to measure a second power spectrum of signals received from said electrode assembly when a user carries out a second exercise simulating muscle activity from which bruxism muscle activity is to be distinguished (such as grimacing), and is operable to display said first and second power spectra to allow a user to identify one or more frequencies that differ strongly between said power spectra for use as said predetermined frequencies. The power spectra may be produced by FFT analysis as described above.

In a further aspect of the invention the device is operable in said set-up mode to measure a first power spectrum of signals received from said electrode assembly when a user carries out a first exercise simulating bruxism muscle activity and to measure a second and/or a third power spectrum of signals received from said electrode assembly when a user carries out a second and/or a third exercise simulating muscle activity from which bruxism muscle activity is to be distinguished. In one embodiment of the invention the second exercise is normal muscle activity such as grimacing. In yet another embodiment the third exercise is when a user when carries out substantially no muscle activity. Furthermore, the device is operable to display said first, second and/or third power spectra to allow a user to identify at least one frequency that differ strongly between said power spectra for use as said predetermined frequencies.

The set-up process may be automated if it is arranged that said device by means of machine computation provides for:
identification of at least one frequency that differ strongly between said power spectra for use as said predetermined frequencies, and
input of at least one of said frequencies for use in said use-mode.

The apparatus may also be configured such that in said set-up mode it registers received signals produced when the user makes no facial movement and establishes therefrom a value of the amplitude at the frequency or frequencies used for bruxism determination that corresponds essentially to noise rather than any significant muscle activity.

Thus, it may be determined that an episode of bruxism is occurring, and a stimulation signal may be triggered, if a sufficiently large amplitude (A) is measured at a frequency or band of frequencies selected over and above the noise value recorded as above at the selected frequency or frequency band. This may be expressed such that an episode of bruxism is detected if a sufficiently large value of Y is produced according to the formula:

$$(A-N)*S>Y;$$

Where:
A=Measured Amplitude at the given frequency
N=Measured Noise at the given frequency
S=Sensitivity The value of 'S' may be adjusted in the set-up to suit an individual user, as may the threshold value of 'Y' above which bruxism is considered to be occurring.

More preferably, a double condition is required to be satisfied, such that:

$$(A_{f1}-N_{f1})*S_{f1}>Y_{f1}$$

and $$(A_{f2}-N_{f2})*S_{f2}>Y_{f2}$$

at the same time, where the subscripts 'f1' and 'f2' respectively indicate values of A, N, S and Y at a first frequency or band of frequencies and a second frequency or band of frequencies, separate from or overlapping with the first. Each frequency or frequency band may be identified by the user or an expert or by automatic machine computation as best reflecting differences in the power spectra of signals received in set-up mode from bruxism simulation as by teeth clenching on the one hand and the generation of potentially confounding signals as by grimacing on the other hand.

In an alternative aspect, the invention includes apparatus for monitoring bruxism activity of a muscle, said apparatus comprising:

an electrode assembly for providing signals indicative of activity of said muscle, means for processing said signals in order to detect said bruxism activity, and means for providing a feedback signal in response to detecting said bruxism activity;

wherein the apparatus is operable in a set-up mode to measure signals indicative of activity of said muscle simulating bruxism and to measure noise signals in the absence of significant activity of said muscle; and wherein said signal processing means determines the amplitude in said signals at a first frequency or band of frequencies and a second frequency or band of frequencies, separate from or overlapping with the first, and activates said means for providing a feedback signal to produce such a feedback signal when a double condition is satisfied, such that:

$$(A_{f1}-N_{f1})*S_{f1}>Y_{f1}$$

and $$(A_{f2}-N_{f2})*S_{f2}>Y_{f2}$$

at the same time, where the subscripts 'f1' and 'f2' respectively indicate values of A, N, S and Y at said first frequency or band of frequencies and at said second frequency or band of frequencies; where Y=a threshold value
A=Measured Amplitude at the given frequency
N=Measured Noise at the given frequency
S=Sensitivity.

Such an apparatus may include all of the features described herein.

In a further aspect of the invention the signal processing means conducts a Fourier transform analysis of said signals to determine the amplitude in said signals at a first frequency or band of frequencies and a second frequency or band of frequencies, separate from or overlapping with the first.

As is known in the art, the feedback signal for correcting bruxism may take many forms including a vibration signal produced in a device worn by the user, a sound signal, or a light signal. However, as described in WO2004/087258 it is preferred that said means for providing a feedback signal provides an electrical stimulation signal to a said electrode assembly. This may be the same electrode assembly or one of two similar such assemblies as is used for gathering the EMG signals, and that is preferred, but it could be a second such assembly used only for the administration of the stimulation signal. The intensity of the feedback signal, whatever its nature, is preferably user adjustable in the set-up mode of the device.

A further object of the invention is to provide that the stimulation signal has the desired effect on bruxism behaviour, for example enough power to have an impact on the temporal muscle. However it is important that the user is not disturbed or wakened from sleep. Preferably the stimulation signal is adjustable to achieve these ends. Therefore a match is needed between the form of the signal and the form of the electrode assembly.

For use with the electrode assembly conformations described herein, it is preferred that said electrical stimulation signal is a biphasic signal which is initiated at a voltage applied to the electrode assembly of not more than 10 volts peak to peak and is raised to a maximum peak to peak voltage at a rate of not more than 500 V/sec, said signal having a duration of not more than 2 sec, a said maximum voltage of not more than 100 volts peak to peak.

Preferably, said biphasic signal has a pulse width of from 50 μsec to 10 msec, more preferably from 50 to 500 μsec, more preferably from 100 to 300 μsec, for instance about 150 μsec.

The signal is preferably initiated at a voltage applied to the electrode assembly of not more than 5 volts peak to peak. The signal preferably increases in intensity from its initial value at a rate of not more than 350 V/sec, more preferably not more than 250 V/sec, for instance between 100 and 250 V/sec, e.g. about 200 V/sec. The duty cycle of the signal may be from 1 to 99%, but is preferably in the range of from 30 to 70%, suitably about 50%.

The invention includes in a second aspect the use of the described apparatus in a method of behavioural modification to correct bruxism or in a method of preventing the occurrence of bruxism, which comprises operating the apparatus in a use mode to receive EMG signals from the temporal muscle, conducting a frequency analysis of such signals, and determining whether a sufficient amplitude is present in said signals at one or more selected frequencies or frequency bands, and generating a feedback signal only when said condition is met. Preferably, said condition includes the detection of the simultaneous presence of a sufficient amplitude at more than one (preferably two) selected frequencies or in more than one (preferably two) selected frequency bands. Said method may further include the operation of the apparatus in the set-up mode described above. In a further aspect of the invention said condition includes the detection of the simultaneous presence of a sufficient amplitude at more than two selected frequencies or in more than two selected frequency bands, such as three selected frequency bands, such as four selected frequency bands, such as five selected frequency bands.

In a further aspect, the invention includes detecting an episode of bruxism which comprises operating the apparatus in a use mode to receive EMG signals from the temporal muscle, conducting a frequency analysis of such signals, and determining whether a sufficient amplitude is present in said signals at one or more selected frequencies or frequency bands. Said method may further include the operation of the apparatus in the set-up mode described above.

In a further aspect, the invention includes a method of setting up apparatus as described herein comprising at least operating the apparatus in a set-up mode to measure a first power spectrum of signals received from said electrode assembly when a user carries out a first exercise simulating bruxism muscle activity and to measure a second power spectrum of signals received from said electrode assembly when a user carries out a second exercise simulating muscle activity from which bruxism muscle activity is to be distinguished, and identifying from a user or expert or automated comparison of said first and second power spectra one or more frequencies that differ strongly between said power spectra for use as measurement frequencies when using the apparatus for monitoring bruxism. Preferred features of said set-up procedure are as described herein.

DRAWINGS

The invention will be further described and illustrated by reference to the accompanying drawings in which:

FIG. 1 shows in plan view a preferred example of an electrode assembly according to the invention;

FIG. 2 shows in plan view a disposable gel patch assembly for use with the electrode of FIG. 1;

FIG. 3 shows a plot of amplitude against time of an electrical stimulation pulse to be applied via the electrode assembly of FIG. 1.

DETAILED DESCRIPTION OF THE INVENTION

Figure 4:
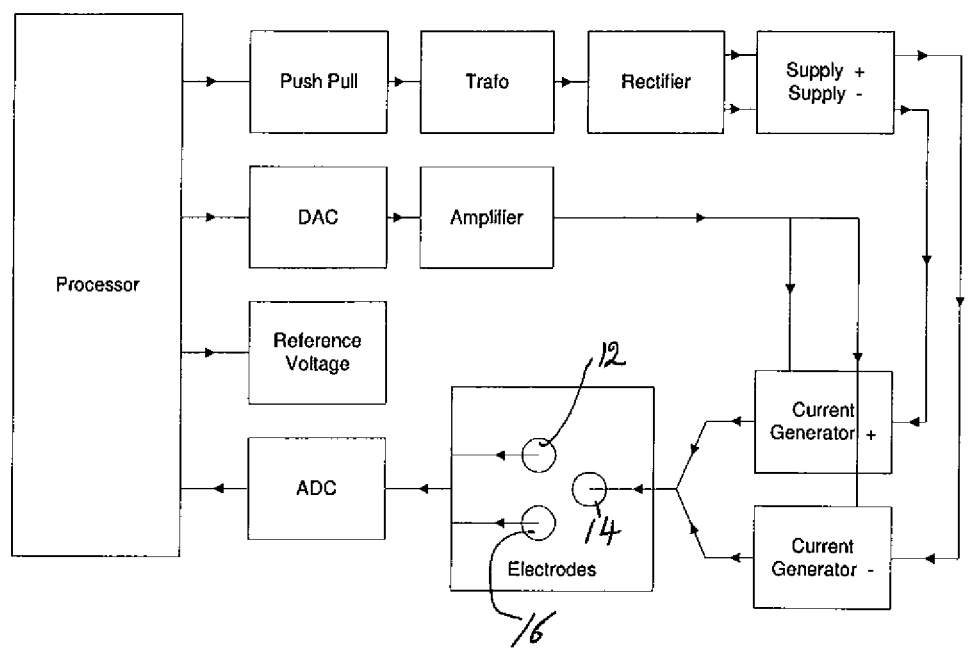
FIG. 4 shows a block circuit diagram of a bruxism monitoring apparatus of the invention.

As shown in FIG. 1, an electrode assembly comprises a substrate 10 in the form of an electrically insulating plastics sheet supporting three metal electrodes 12, 14 and 16, each being circular in plan form and being of diameter 'a', which is suitably 5 mm. The thickness of the illustrated electrodes is about 3 mm. The electrodes are spaced by a distance between centres 'b', which as shown is about 16 mm. The centres of the electrodes fall on an arc of a circle of radius 'c', which as shown is about 70 mm. Each electrode 12,14,16 has a respective connecting wire 18 leading across the surface of the substrate 10 to a common exit point where the wires a bundled together for mutual support as a cable 19.

The gel patch assembly 20 shown in FIG. 2 also comprises an electrically insulating substrate 22 of plastics sheet which matches in size and shape the substrate 10 of the electrode assembly. On both faces, the substrate 20 carries a peelable adhesive for adhering one face to the substrate 10 of the electrode assembly and for adhering the opposite face to the skin of a user.

Three apertures 22, 24 and 26 are provided in the substrate 20, e.g. of 7 mm diameter, for receiving the respective electrodes (shown as faint lines within the apertures). The apertures are each covered by an electrically conductive gel patch 28 of circular form sufficient in diameter to span the apertures and mounted on the substrate 20, e.g. 10 mm. These connect in use between the electrodes and the skin.

For storage prior to use, each face of the gel patch assembly is covered by protective sheet which is peeled off prior to use. The user first peels away the protective sheet from the face of the gel patch assembly that is to contact the electrode assembly and mounts the two together. The user then removes the protective sheet from the opposite face and mounts the electrode assembly with the gel patch assembly onto the skin over the temporal muscle.

The electrode assembly in use may be connected to apparatus for monitoring bruxism as described in WO 2004/087258. Upon an episode of bruxism being detected, the apparatus generates an electrical stimulation pulse as a feedback signal which is directed to the skin of the patient through the electrode assembly. Optionally, a respective electrode assembly may be provided for each side of the user's head and if both are not used for sensing EMG signals, one may be used exclusively for administering the stimulation pulses and the other may be used for sensing the EMG signals.

The form of the stimulation pulse should be tailored to suit the size and layout of the electrodes. In FIG. 3 there is shown a pulse form that is ideally adapted to the electrode assembly of FIG. 1. The pulses start gently, so as to avoid a sudden shock which might awaken the user, suitably starting from zero volts as shown. The parameters of the illustrated pulse are as follows:
Start voltage=0 V (peak-peak)
End voltage=76 V (peak-peak)
Pulse width=250 μsec
Pulse train duration=400 msec
Inter-pulse spacing=250 μsec
Duty cycle (pulse)=50%
Pulse set spacing=5 msec
Duty cycle (pulse set)=10%

In this specific embodiment of the apparatus each individual pulse within the stimulation pulse has a duration of 250 μsec and positive voltage pulses of that duration alternate with negative voltage pulses of the same duration. There is a pause between positive and negative pulses of 250 μsec, producing a duty cycle of 50%.

A single stimulation pulse of this ramped voltage form may be administered each time a bruxism episode is detected by the apparatus. The apparatus may contain user operable means for adjusting the end voltage, normally by setting a desired end current, preferably this provides adjustment within a range of at least 60-80V, more preferably 50-90V, for instance 0-100 V. The start voltage/current will normally be fixed (generally at 0 V), but may be adjustable.

As shown in FIG. 4, the circuitry of apparatus of the invention is configured to receive EMG signals from the electrodes of the electrode assembly and to process these in a microprocessor ('processor') to determine that an episode of bruxism is taking place, whereupon sensing of the EMG is suspended and via two current generator modules a current is impressed on the electrodes by the application of the voltage pulse of FIG. 3. The apparatus is powered by a small battery, the output from which is chopped and transformed to high voltage and is stored in high voltage capacitors. A complete stimulation cycle typically comprises about 80 pulse cycles, positive and negative pulses spaced by a pause making up each pulse cycle. The pulse cycles slowly increase in intensity up to a programmed current value. Between each pulse cycle, the energy for the next pulse cycle is pumped to the high voltage capacitors.

The connection of the electrodes to the skin is monitored at frequent intervals and the application of the stimulation is blocked if no sufficient connection is present. The processor shown in FIG. 4 carries out FFT analysis of the signals received from the electrode assembly so as to produce a power spectrum therefrom. In a set-up mode, signals may be registered that arise from the user being relaxed (without significant activity of the temporal muscle), then with the user making deliberate facial muscle activities such as may be produced in grimacing which need to be distinguished in the use of the apparatus from signals produced in bruxism, and then with the user simulating bruxism by clenching their teeth strongly. From the FFT analysis of the signals produced by grimacing compared to those produced by clenching, frequencies may be identified either by user or expert inspection of the power spectra or automatically in the apparatus that strongly differentiate these activities for the individual user. Alternatively however, the apparatus may be pre-programmed to use frequencies that work well for most users.

Signals received when the user is relaxed may be used to establish a noise value at the relevant frequencies, which may be taken into account in determining in the use mode whether there is a sufficient amplitude detected to indicate bruxism.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

The apparatus according to the invention is preferably suited for monitoring muscle activity related to bruxism, said muscle activity detected from the temporal muscle, the masseter muscle and/or both the temporal and the masseter muscle.

Correspondingly the method according to the invention is also suited for monitoring activity of the temporal muscle, the masseter muscle and/or both the temporal and the masseter muscles.

The invention claimed is:

1. Apparatus for monitoring muscle activity related to bruxism, said apparatus comprising:
    an electrode assembly for providing signals indicative of said muscle activity,
    means for processing said signals in order to detect said bruxism, and
    means for providing a feedback signal to said electrode assembly in response to detecting said bruxism;
    wherein said electrode assembly comprises three electrodes in a fixed spatial relationship one to another, each electrode having a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm,
    wherein the electrodes are arranged such that centres of said electrodes lie on a line which is an arc of a circle having a radius of from 60-200 mm,
    wherein the contact areas of the electrodes extend along or on said line a distance of from 3 to 7 mm from one side to an opposite side of the electrode contact area, and
    wherein the contact areas of the electrodes extend transversely of said line by a distance of from 3 to 7 mm from one side to an opposite side of the electrode contact area.

2. Apparatus as claimed in claim 1, wherein the maximum distance along said line from an edge of a first said electrode contact area to an opposite edge of the furthest away of the other two electrode contact areas is from 20 to 50 mm.

3. Apparatus as claimed in claim 1, wherein the contact areas of the electrodes are arranged in a triangular arrangement in which the longest side of the triangle so defined is not more than 40 mm.

4. Apparatus as claimed in claim 1, wherein said means for processing said signals in order to detect said bruxism measures the amplitude of EMG signals received from said electrode assembly at one or more predetermined frequencies.

5. Apparatus as claimed in claim 4, wherein said apparatus is operable in a set-up mode and in a use mode and in said set-up mode is configured to accept an input defining said one or more predetermined frequencies and in said use mode detects bruxism episodes by measuring the amplitude of EMG signals at said one or more frequencies received from said electrode assembly.

6. Apparatus as claimed in claim 5, wherein said apparatus is operable in said set-up mode to measure a first power spectrum of signals received from said electrode assembly when a user carries out a first exercise simulating bruxism muscle activity and to measure a second and/or a third power spectrum of signals received from said electrode assembly when a user carries out a second and/or a third exercise simulating muscle activity from which bruxism muscle activity is to be distinguished.

7. Apparatus as claimed in claim 6, wherein the second power spectrum of signals received from said electrode assembly is measured when a user carries out normal muscle activity and/or wherein the third power spectrum of signals received from said electrode assembly is measured when a user carries out substantially no muscle activity.

8. Apparatus is claimed in claim 6, operable to display said first, second and/or third power spectra to allow a user to identify at least one frequency that differ strongly between said power spectra for use as said predetermined frequencies.

9. Apparatus is claimed in claim 6, wherein said apparatus by means of machine computation provides for:
    identification of at least one frequency that differ strongly between said power spectra for use as said predetermined frequencies, and
    input of at least one of said frequencies for use in said use-mode.

10. Apparatus as claimed in claim 1, where in the feedback signal is applied to correct bruxism.

11. A method for monitoring activity of the temporal muscle, said method comprising the steps of:
    providing signals indicative of activity of said temporal muscle by means of an electrode assembly having three electrodes in a fixed spatial relationship wherein each electrode has a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm, and wherein the electrodes are arranged such that centres of said electrodes lie on a line which is an arc of a circle having a radius of from 60-200 mm,
    wherein the contact areas of the electrodes extend along or on said line a distance of from 3 to 7 mm from one side to an opposite side of the electrode contact area, and
    wherein the contact areas of the electrodes extend transversely of said line by a distance of from 3 to 7 mm from one side to an opposite side of the electrode contact area,
    processing said signals in order to detect temporal muscle activity, and
    providing a feedback signal to said electrode assembly in response to detecting the temporal muscle activity.

12. A method according to claim 11, whereby processing of said signals in order to detect temporal muscle activity measures the amplitude of EMG signals received from said electrode assembly at one or more predetermined frequencies.

13. A method according to claim 12, whereby said one or more predetermined frequencies are defined in a set-up mode which is configured to accept an input, and whereby temporal muscle activity episodes are detected in a use-mode by measuring the amplitude of EMG signals at said one or more frequencies received from said electrode assembly.

14. A method according to claim 13, whereby a first and a second and/or a third power spectra of signals are measured in said set-up mode, said first power spectrum of signals received from the electrode assembly when the user carries out a first temporal muscle activity and said second and/or third power spectrum of signals received from the electrode assembly when the user carries out a second and/or a third temporal muscle activity from which the first temporal muscle activity is to be distinguished.

15. A method according to claim 14, wherein the activity of the temporal muscle is bruxism or simulation of bruxism.

16. A method according to claim 14, wherein the second power spectrum of signals received from said electrode assembly is measured when a user carries out normal temporal muscle activity.

17. A method according to claim 14, wherein the third power spectrum of signals received from said electrode assembly is measured when a user carries out substantially no temporal muscle activity.

18. A method according to claim 14, whereby said first, second and/or third power spectra are displayed to allow a user to identify at least one frequency that differ strongly between said power spectra for use as said predetermined frequencies.

19. A method according to claim 13, whereby said at least one or more predetermined frequencies are automatically entered for use in said use-mode.

20. A method according to claim 11, wherein the feedback signal is provided to reduce the activity of the temporal muscle.

\* \* \* \* \*